US00PP24682P3

(12) United States Plant Patent
Reijm

(10) Patent No.: US PP24,682 P3
(45) Date of Patent: Jul. 22, 2014

(54) *DRACAENA* PLANT NAMED 'REIJDRAMAS'

(50) Latin Name: *Dracaena fragrans*
Varietal Denomination: Reijdramas

(71) Applicant: Pieter Johannes Reijm, Nieuwerkerk aan den Ijssel (NL)

(72) Inventor: Pieter Johannes Reijm, Nieuwerkerk aan den Ijssel (NL)

(73) Assignee: Kwekerij Reijm Nieuwerkerk B.V. (NL)

( * ) Notice: Subject to any disclaimer, the term of this patent is extended or adjusted under 35 U.S.C. 154(b) by 50 days.

(21) Appl. No.: 13/694,235

(22) Filed: Nov. 8, 2012

(65) Prior Publication Data
US 2014/0130221 P1 May 8, 2014

(51) Int. Cl.
*A01H 5/00* (2006.01)

(52) U.S. Cl.
USPC ..... Plt./383

(58) Field of Classification Search
USPC ..... Plt./383
See application file for complete search history.

*Primary Examiner* — Kent L Bell
(74) *Attorney, Agent, or Firm* — Cassandra Bright

(57) ABSTRACT

A new and distinct *Dracaena* cultivar named 'Reijdramas' is disclosed, characterized by dark green leaves with strong yellow-green center stripes. Plants are large and vigorous, and produce very glossy foliage. The new variety is a *Dracaena*, typically produced as an ornamental plant.

1 Drawing Sheet

Latin name of the genus and species: *Dracaena fragrans*.
Variety denomination: 'Reijdramas'.

BACKGROUND OF THE INVENTION

The new cultivar is the product of chance discovery. The new variety originated as a naturally occurring, whole plant mutation of the unpatented variety *Dracaena fragrans* 'Massangeana'.

The new variety was discovered by the inventor, Pieter Johannes Reijm, a citizen of the Netherlands, in March 2011, in a commercial nursery in Nieuwerkerk, the Netherlands. After identifying the new variety as a potentially interesting selection, the inventor continued confidential testing and propagation of 'Reijdramas', assessing the stability of the unique characteristics of this variety.

Asexual reproduction of the new cultivar 'Reijdramas' was first performed at the commercial nursery in Nieuwerkerk, the Netherlands by vegetative cuttings in November 2011. Access to all plants was restricted, as plants were kept in an area not open to the public. Through subsequent propagation by vegetative cuttings, multiple generations have been reproduced, which have shown that the unique features of this cultivar are stable and reproduced true to type.

SUMMARY OF THE INVENTION

The cultivar 'Reijdramas' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Reijdramas'. These characteristics in combination distinguish 'Reijdramas' as a new and distinct *Dracaena* cultivar:

1. Large, vigorous plant
2. Distinctive dark green foliage with yellow-green center stripes.
3. Very glossy foliage.

PARENT COMPARISON

Plants of the new cultivar 'Reijdramas' are similar to the parent, *Dracaena fragrans* 'Massangeana' in most horticultural characteristics. Plants of the new variety, however, are overall larger than plants of 'Massangeana'. The new variety produces foliage which grows more upright, and is both longer and wider than foliage of 'Massangeana'. Additionally, the distinctive lighter colored striping in the center of the leaves of the new variety is wider, and lighter colored than the foliage striping of the parent variety.

COMMERCIAL COMPARISON

'Reijdramas' can be compared to the commercial variety *Dracaena fragrans* 'Mass Coast', U.S. plant patent application Ser. No. 13/573,425. The new variety, however, produces leaves that are glossier than 'Mass Coast'. Additionally, plants of the new variety grow faster than plants of 'Mass Coast'.

BRIEF DESCRIPTION OF THE PHOTOGRAPH

The accompanying photograph in FIG. 1 illustrates in full color a typical plant of 'Reijdramas' grown in a commercial greenhouse in Nieuwerkerk, the Netherlands. This plant is approximately 12 months old, shown planted in a 24 cm container. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001, except where general terms of ordinary dictionary significance are used. The following observations and measurements describe 'Reijdramas' plants grown in a greenhouse in Munster, The Netherlands. A steady temperature of approximately 20° C. at night and 20° C. during the day was maintained. No artificial light, photoperiodic treatments were given to the plants. The plant was shaded if the sun was shining on it. Measurements and numerical values represent averages of typical plant types.

Botanical classification: *Dracaena fragrans* 'Reijdramas'.

PROPAGATION

Time to initiate rooting: About 4 weeks at approximately 20° C. 6 weeks for full rooting.

Root description: Moderately thick, moderately fibrous, not fleshy, Yellow-White 158C.

PLANT

Age of plant described: 1 year.
Pot size of plant described: 24 cm pot.
Growth habit: Upright.
Height: Approximately 99.7 cm.
Plant spread: Approximately 106.0 cm.
Growth rate: Moderate to vigorous, approx. 15 cm per month.
Branching characteristics: Not free branching, typically growing with one main stem from the base. Will only develop lateral branches after pinching or pruning.
Diameter of stem: Approximately 2.4 cm.
Internode length: Average 0.5 cm.
Texture of stem: Smooth, moderately glossy.
Color of stem: Yellow-green, near RHS 145D and 150D.
Stem strength: Very strong.
Number of leaves per stem: Average 34.

FOLIAGE

Leaf:
- *Arrangement*.—Alternate (spirally).
- *Average length*.—Approximately 73.1 cm.
- *Average width*.—Approximately 11.2 cm.
- *Shape of blade*.—Lorate.
- *Aspect*.—Leaves in an average angle of 55° to stem (=0°=vertical); leaf blades curved horizontal. Leaf blades moderately undulate, slightly twisted.
- *Apex*.—Acute with a pungent (not sharp) outer tip.
- *Base*.—Broad cuneate.
- *Attachment*.—Sheathing.
- *Margin*.—Entire.
- *Texture of top surface*.—Smooth, glossy.
- *Texture of bottom surface*.—Smooth, slightly glossy.

Color:
- *Young foliage upper side*.—Green near RHS 143A. Axially (lengthways) striped yellow-green; near RHS 150C.
- *Young foliage under side*.—Green; near RHS 137D. Axially (lengthways) striped yellow-green; near RHS 145A and 150C.
- *Mature foliage upper side*.—Green; near RHS 141A but darker. Axially (lengthways) striped yellow-green; near RHS N144D.
- *Mature foliage under side*.—Green; near RHS 137D, Axially, (lengthways) striped yellow-green; near RHS N144C.

Venation:
- *Type*.—Parallel.
- *Color*.—Upperside: Indistinguishable from leaf blade. Underside: Indistinguishable from leaf blade.

Sheath:
- *Average length*.—Approximately 6.0 cm.
- *Average width*.—Approximately 2.4 cm.
- *Color*.—Yellow-green; near RHS 144D.
- *Texture*.—Smooth, very glossy.

OTHER CHARACTERISTICS

Flower production: Not observed.

Disease resistance: Neither resistance nor susceptibility to normal diseases and pests of *Dracaena* has been observed.

Drought tolerance and temperature tolerance: Moderately high drought resistance, good heat resistance to at least 40° C.

Fruit/seed production: Not observed.

What is claimed is:

1. A new and distinct cultivar of *Dracaena* plant named 'Reijdramas' as herein illustrated and described.

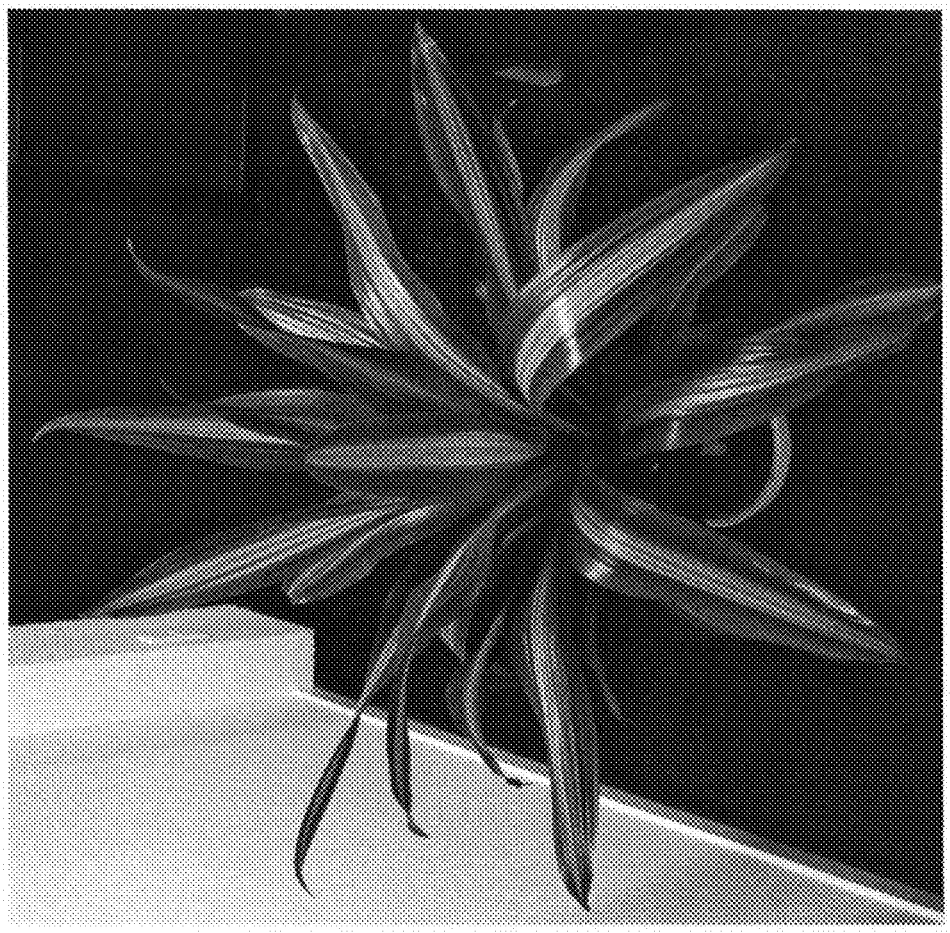

* * * * *